US005395380A

United States Patent [19]

Berkovich

[11] Patent Number: 5,395,380

[45] Date of Patent: Mar. 7, 1995

[54] DEVICE FOR REMOVING BLACKHEADS

[76] Inventor: Tamara Berkovich, 116 N. Wetherly Dr., Suite 115, Los Angeles, Calif., 90048

[21] Appl. No.: 163,363

[22] Filed: Dec. 2, 1993

[51] Int. Cl.[6] ........ A61B 17/56

[52] U.S. Cl. ........ 606/131; 132/286; 601/17; 604/290

[58] Field of Search ........ 606/131, 134; 30/324, 30/325; 604/290, 289; 132/286; 601/17

[56] References Cited

U.S. PATENT DOCUMENTS

| | | | |
|---|---|---|---|
| D. 41,822 | 10/1911 | Ridout | 30/324 |
| 50,133 | 1/1917 | Johnson | 30/325 |
| 575,356 | 1/1897 | Kloss | 606/131 |
| 769,412 | 9/1904 | Sidway | 30/325 |
| 896,338 | 12/1908 | Tolman | 606/131 |
| 906,805 | 8/1908 | Tolman | 606/131 |
| 911,828 | 2/1909 | Pither | 30/325 |
| 1,488,463 | 4/1924 | Abram | 30/325 |
| 4,291,685 | 9/1981 | Taelman | 601/17 |
| 4,425,711 | 1/1984 | Wood et al. | 30/324 |
| 4,655,232 | 4/1987 | Ficke | 601/17 |

*Primary Examiner*—Paul J. Hirsch

[57] ABSTRACT

A device for removing blackheads from pores in the skin having a elongated handle with a spoon shaped portion mounted on one end thereof, the spoon having multiple small holes piercing therethrough. Also covered is method for using the device to remove blackheads.

6 Claims, 1 Drawing Sheet

DEVICE FOR REMOVING BLACKHEADS

BACKGROUND

The present invention relates to a tool for removing blackheads or sebum from the skin.

Sebum is a fatty lubricant matter secreted by sebaceous glands of the skin. A blackhead is created when a small plug of sebum blocks the duct of a sebaceous gland often occurring on the face according to Webster's New Collegiate Dictionary. In order to remove the plug two methods are commonly used. The first method which is used is to squeeze the skin adjacent to the blackhead. The second method is to use a blackhead removal tool commercially available. The blackhead removal tool consists of a handle with a 7 mm plate on at least one end. The plate which can have a slight indentation has a hole of about 2.0 to 3.0 mm in diameter positioned within that plate. The plate is positioned over the clogged pore with the walls of the hole surrounding the blackhead and depressed directly downward onto the skin. The plate is about 1 mm thick so as to withstand the pushing pressure without bending the tool.

The first method tends to be painful and can leave pock marks on the user's face. The second method while being less painful is less effective. Thus there is a need for an improved tool and method for removing blackheads.

SUMMARY

These needs are met by the present invention which comprises a tool having an elongated handle with a spoon-like end and a multitude of holes through the spoon portion. To use the device press with a slight sliding and twisting action at an angle to the skin adjacent to the blackhead. This motion will depress the skin surrounding the blackhead and force the plug to rise above the skin level, where it can penetrate the spoon holes and be removed when the tool is twisted or slid across the skin and over the blackhead.

DRAWINGS

These and other features, aspects and advantages of the present invention will become better understood with reference to the following description, appended claims and accompanying drawings, where:

Figure 1:
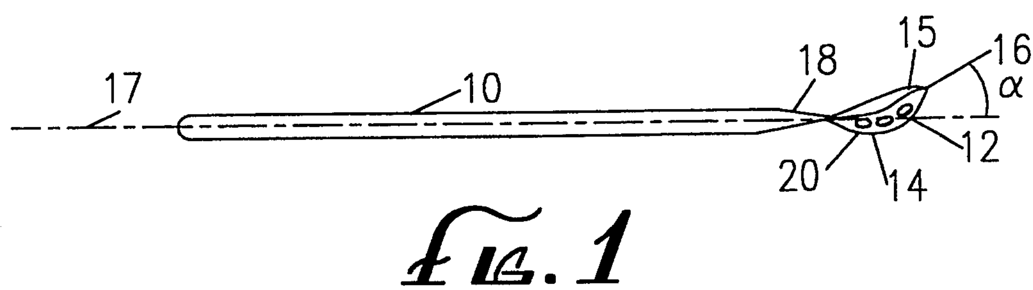
FIG. 1 shows the side view of the invention.
Figure 2:
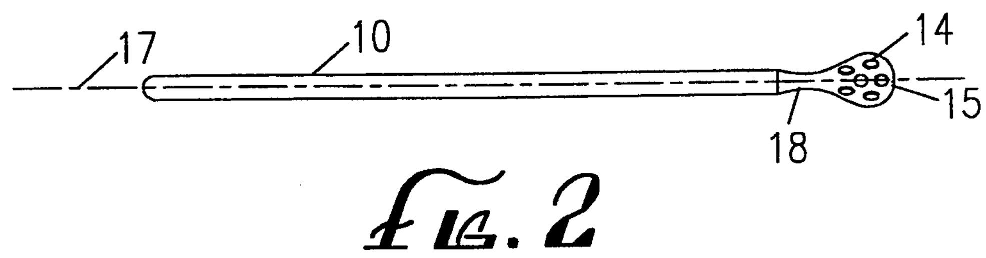
FIG. 2 shows the top view of the invention.

DESCRIPTION OF THE PREFERRED EMBODIMENTS:

FIGS. 1 and 2 show a new and improved tool embodying features of the invention. The tool is composed of an elongated handle 10 having a spoon shaped region 12 mounted on one end. Located in the spoon shaped region 12 are several holes 14.

The handle 10 is shown as a long narrow rod. The rod can be formed with a smooth or a many sided cylindrical surface which can have serrations or grooves to aid in grasping. Preferably the handle 10 has a length adequate to be easily grasped in the hand of the user rather than being held only by a few fingers. The tool can be produced from metal, such as used in dental or surgical equipment or from a structural plastic. The material must be safe for use in contact with the skin, strong enough so that it will not break when pressure is applied during normal use and capable of being polished so that sharp edges are not formed when holes are cut through it.

A preferred design has the terminal portion 15 of the spoon 12 at an angle $\alpha$ of about 30 to 55 degrees to a central axis 17 through the length of the handle with the tip 16 being elevated above the plane of the handle 10. A more preferred embodiment has the angle of the spoon 12 at 45 degrees to the axis 17. An angle of the spoon 12 which best fits the skin curvatures works best.

The depth of the spoon 12, the measure from the central deepest area 20 of the spoon 12 to the spoon edge 16, ranges from 1/16" to 3/16". A preferred thickness of the spoon 12 is about 0.5 mm.

The multitude holes 14 formed in the spoon range in size from 0.8 mm to about 2 mm in diameter. In contrast the prior art products have a single hole of about 2 mm to about 3 mm in diameter. The tool shown in FIGS. 1 and 2 have multiple holes randomly arranged across the spoon's surface covering from 20% to 65% of the surface. This arrangement of holes allows the tool to be used on an area of the skin while the single hole device of the prior art can only be used on a single blackhead at a time and must be constantly repositioned.

To use the tool described above, a section of skin to be treated is identified. While grasping the handle 10 firmly the spoon is placed adjacent to the identified area with the tip 16 only making a slight or no contact with the skin. The spoon is then worked across the skin in the direction of the handle in a sliding, rocking or twisting manner depressing the skin under the spoon as it is moved, forcing the blackhead up and out of the pores so it can be collected in and passed through the holes 14 and into the central portion of the spoon. In this manner large areas of skin can be treated in a rapid and consistent manner.

It is possible to improve the procedure by first applying skin conditioners, such as skin softeners and/or pore openers to the area to be treated followed by antiseptics, antibiotics or other pharmaceutical treatments and then, after the treatment, astringents or other pore closing compounds to close and seal the now empty pores.

In a particular preferred embodiment the tool has a handle about 12 mm in length, the spoon is oval shaped with a major axis of about 1.5 cm and a minor axis of about 0.8 mm and a spoon depth of about 2/16". Thirteen holes ranging in size from about 2 mm to 2.5 mm randomly pierce the spoon surface with no hole being closer then 0.1 mm to the edge of the spoon. The total area of the holes comprise about 45% of the surface of the spoon.

Although a tool incorporating the present invention has been described in considerable detail with reference to certain preferred versions and uses thereof, other versions and uses are possible. For example, the tool can be used for other skin conditions which result in pore blockages such as acne. Therefore, the spirit and scope of the appended claims should not be limited to the description of the preferred versions contained herein.

What is claimed is:

1. A process for removing sebum from blocked pores in a skin surface comprising:

a) gripping an elongated handle of a pore cleaning tool, said tool having a spoon shaped portion of a defined thickness mounted to said handle, the spoon shaped portion having a convex surface with multiple holes penetrating through the convex surface and the thickness of the spoon portion, the holes being dispersed across the convex surface, b) pressing the convex surface against a skin surface at a point spaced from the blocked pores, depressing the skin under the spoon portion, and c) advancing the convex surface across the skin area containing the blocked pores while maintaining pressure against the skin so that the skin surface in front of the advancing convex surface is progressively depressed, the sebum being forced out of the pores and through the holes in the spoon shaped portion, said process being performed without the need to visualize through a hole in the spoon shaped portion the pores containing blocking sebum.

2. The method of claim 1 wherein a skin conditioner is applied to the skin before the tool is used.

3. The method of claim 2 wherein the skin conditioner is chosen from the group containing a pore opener and a skin softener.

4. The method of claim 1 wherein a moisturizer is applied to the skin after the skin conditioner and before the tool is used.

5. The method of claim 4 wherein a pore closer is applied to the skin after the pore cleaning tool has been used.

6. The process of claim 1 wherein the spoon shaped portion has holes randomly located therein, the area of the holes being about 20% to about 65% of the surface area of the spoon shaped portion.

* * * * *